United States Patent
Harmer et al.

(10) Patent No.: US 7,829,706 B2
(45) Date of Patent: Nov. 9, 2010

(54) IONIC LIQUIDS

(75) Inventors: Mark Andrew Harmer, Landenberg, PA (US); Christopher P. Junk, Wilmington, DE (US); Jemma Vickery, Hants (GB)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 12/472,434

(22) Filed: May 27, 2009

(65) Prior Publication Data

US 2009/0234119 A1 Sep. 17, 2009

Related U.S. Application Data

(62) Division of application No. 11/523,885, filed on Sep. 20, 2006, now Pat. No. 7,544,813.

(60) Provisional application No. 60/719,370, filed on Sep. 22, 2005.

(51) Int. Cl.
*C07D 239/24* (2006.01)
*C07D 233/54* (2006.01)

(52) U.S. Cl. ................................... 544/242

(58) Field of Classification Search ............ None
See application file for complete search history.

(56) References Cited

U.S. PATENT DOCUMENTS

| 3,555,080 | A | 1/1971 | Resnick |
| 5,827,602 | A | 10/1998 | Koch et al. |
| 6,720,459 | B2 | 4/2004 | Sunkara et al. |
| 7,544,813 | B2 * | 6/2009 | Harmer et al. ............ 548/335.1 |

FOREIGN PATENT DOCUMENTS

| EP | 0897950 A2 | 2/1999 |
| WO | 03028882 A1 | 4/2003 |
| WO | 2006084262 A1 | 8/2006 |

OTHER PUBLICATIONS

Rogers, Robin D. and Seddon, Kenneth R., Ionic Liquids-Solvents of the Future?, Science, vol. 302, Oct. 31, 2003.
Wasserscheid, Peter et al, Hydrogensulfate and Tetrakis(hydrogensulfato)borate Ionic Liquids: Synthesis and Catalytic Application in Highly Bronsted-Acidic Systems for Friedel-crafts Alkylation, Green Chemistry, 2002, 4, pp. 134-138.
Merrigan, Travis L. et al, New Fluorous Ionic Liquids Function as Surfactants in Conventional Room-Temperature Ionic Liquids, Chem. Commun., 2000, pp. 2051-2052.
Rudyuk, Vitalij V. et al, N-polyfluoroethyl and N-2-chlorodifluorovinyl Derivatives of Azoles, Journal of Fluorine Chemistry 125 (2004), pp. 1465-1471.
Wasserscheid & Keim, Ionic Liquids-New "Solutions" for Transition Metal Catalysis, Angew. Chem. Int. Ed. 2000, 39, pp. 3772-3789.
Sheldon, Roger, Catalytic Reactions in Ionic Liquids, Chem. Commun, 2001, pp. 2399-2407.
Koshar, R. et al, Preparation of B-H-perfluoro Alkanesulfonic Acids, J. Am. Chem. Soc., vol. 75, 1953, pp. 4595-4596.
Huang, W. et al., "Perfluoro and Polyfluorosulfonic Acids", Database CA [Online] Chemical Abstracts Service, Columbus, Ohio, XP002412172, Retrieved From STN Database Accession No. 1983:34194 Abstract and Huaxue Xuebau, vol. 40, No. 9, 1982, pp. 821-827.
Coffman D. D. et al., "Addition Reactions of Tetrafluoroethylene" Journal of Organic Chemistry, American Chemical Society, Easton, US, No. 14, 1949, pp. 747-753.
Shiflett, Mark B., et al., "Solubility and Diffusivity of Difluoromethane in Room-Temperature Ionic Liquids", Database CA [Online] Chemical, Columbus Ohio, XP002412173 Retrieved From STN Database Accession No. 2006:75448 Abstract & Journal of Chem & Engg Data, 51(2), 483-495, ISSN: 0021-9568, 2006.
Shiflett, Mark B., et al., "Solubility and Diffusivity of 1,1,2,2-tetrafluoroethane in room-temperature ionic liquids", Database CA [Online] Chemical, Columbus Ohio, XP002412174 Retrieved From STN Database Accession No. 2006:253906 Abstract & Fluid Phase Equilibria vol. 242 No. 2, 2006, pp. 220-232.
Liu, Jintao et al, 3-oxa Perfluorononyl Fluorocarbon Surfact, Its Synthesis and Application, Database CA [Online] Columbus, OH, XP002412175 Retrieved From STN Database Accession No. 2005:414483, Abstract & CN 1 431 037 CN (Shanghai Inst. of Org. Chem., Chinese Academy of Sciences) Jul. 23, 2003.
Del Sesto, R. E. et al, "Tetraalkylphosphonium-Based Ionic Liquids", Journal of Organometallic Chemistry, Elsevier-Sequoia S.A., Laussanne, CH, vol. 690, No. 10, May 16, 2005, pp. 2536-2542.

* cited by examiner

*Primary Examiner*—Fiona T Powers

(57) ABSTRACT

The present invention relates to compositions of matter that are ionic liquids, the compositions comprising any of eleven cations combined with any of three fluorinated sulfonated anions. Compositions of the invention should be useful as solvents and, perhaps, as catalysts for many reactions, including aromatic electrophilic substitution, nitration, acylation, esterification, etherification, oligomerization, transesterification, isomerization and hydration.

2 Claims, No Drawings

IONIC LIQUIDS

FIELD OF INVENTION

This invention relates to compositions of matter that are useful as ionic liquids.

BACKGROUND OF THE INVENTION

Ionic liquids are liquids composed of ions that are fluid around or below 100 degrees C. (Science (2003) 302:792-793). Ionic liquids exhibit negligible vapor pressure, and with increasing regulatory pressure to limit the use of traditional industrial solvents due to environmental considerations such as volatile emissions and aquifer and drinking water contamination, much research has been devoted to designing ionic liquids that could function as replacements for conventional solvents.

The present invention provides novel compositions comprising fluorinated anions that are useful as ionic liquids. Fluorous ionic liquids have been described. For example, Merrigan, et al. (Chem. Comm. (2002) 2051-2052) describe imidazole-derived ionic liquids having fluorous tails, and Wasserscheid, et al. (Green Chemistry (2002) 4:134-138) describe the synthesis of imidazolium-derived ionic liquids having a bis(trifluoromethanesulfonato)amide anion. In addition, Rudyuk, et al. describe the synthesis of N-polyfluoroethyl and N-2-chlorodifluorovinyl derivatives of azoles, such as imidazole, pyrazole and triazole.

SUMMARY OF THE INVENTION

In its broadest aspect, the present invention relates to a composition of matter of the Formula $Z^+A^-$, wherein $Z^+$ is a cation selected from the group consisting of the following eleven cations:

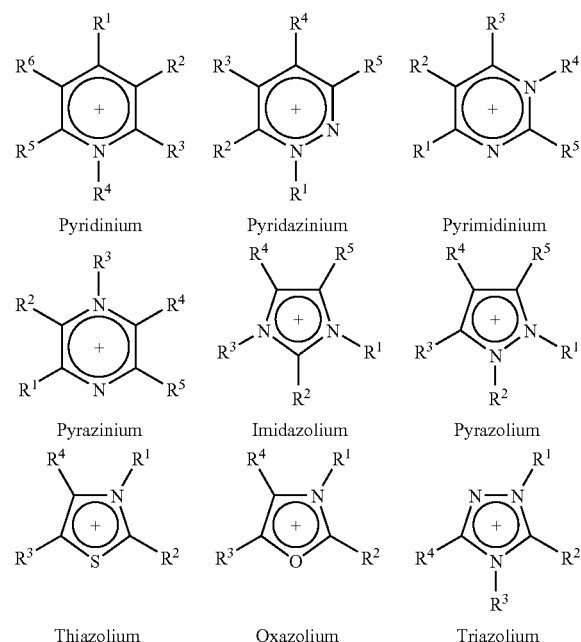

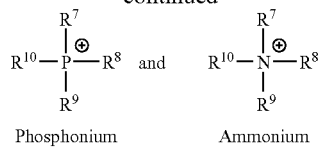

and $A^-$ is selected from the group consisting of the following three anions:

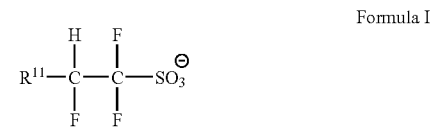

Formula I

Formula II

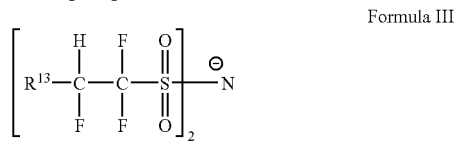

Formula III wherein the R-groups are defined as in the detailed description.

DETAILED DESCRIPTION OF THE INVENTION

The present invention relates to novel compositions comprising fluorinated, sulfonated anions. Compositions of the invention should be useful as solvents and, perhaps, as catalysts for many reactions, including aromatic electrophilic substitution, nitration, acylation, esterification, etherification, oligomerization, transesterification, isomerization and hydration.

Definitions

In this disclosure, a number of terms and abbreviations are used. The following definitions are provided.

By "ionic liquid" is meant organic salts that are fluid around or below 100 degrees C.

By "fluoroalkyl" is meant an alkyl group wherein at least one member selected from the hydrogens has been replaced by fluorine. By "perfluoroalkyl" is meant an alkyl group wherein all of the hydrogens have been replaced by fluorines.

By "alkoxy" is meant a straight-chain or branched alkyl group bound via an oxygen atom. By "fluoroalkoxy" is meant an alkoxy group wherein at least one member selected from the hydrogens has been replaced by fluorine. By "perfluoroalkoxy" is meant an alkoxy group wherein all of the hydrogens have been replaced by fluorines.

By "halogen" is meant bromine, iodine, chlorine or fluorine.

By "heteroaryl" is meant an aryl group having one or more heteroatoms.

When referring to an alkane, alkene, alkoxy, fluoroalkoxy, perfluoroalkoxy, fluoroalkyl, perfluoroalkyl, aryl or heteroaryl, the term "optionally substituted with at least one member selected from the group consisting of" means that one or more hydrogens on the carbon chain may be independently substituted with one or more of at least one member of the group. For example, substituted $C_2H_5$ may be, without limitations, $CF_2CF_3$, $CH_2CH_2OH$ or $CF_2CF_2I$.

The expression "C1 to Cn straight-chain or branched", where n is an integer defining the length of the carbon chain, is meant to indicate that C1 and C2 are straight-chain, and C3 to Cn may be straight-chain or branched.

The present invention relates to compositions of matter of the Formula $Z^+A^-$, wherein $Z^+$ is a cation selected from the group consisting of:

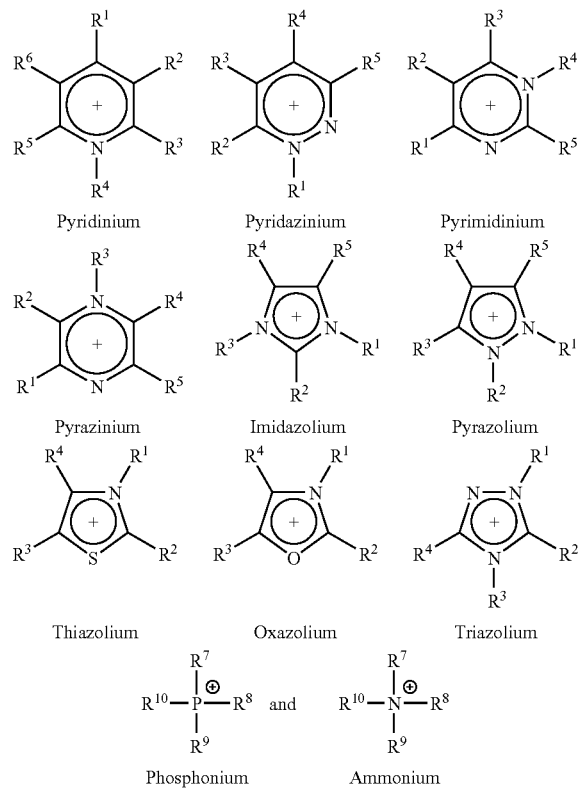

wherein $R^1$, $R^2$, $R^3$, $R^4$, $R^5$ and $R^6$ are independently selected from the group consisting of:
(i) H
(ii) halogen
(iii) —$CH_3$, —$C_2H_5$, or $C_3$ to $C_{25}$, preferably $C_3$ to $C_{20}$, straight-chain, branched or cyclic alkane or alkene, optionally substituted with at least one member selected from the group consisting of Cl, Br, F, I, OH, $NH_2$ and SH;
(iv) —$CH_3$, —$C_2H_5$, or $C_3$ to $C_{25}$, preferably $C_3$ to $C_{20}$, straight-chain, branched or cyclic alkane or alkene comprising one to three heteroatoms selected from the group consisting of O, N and S, and optionally substituted with at least one member selected from the group consisting of Cl, Br, F, I, OH, $NH_2$ and SH;
(v) $C_6$ to $C_{25}$ unsubstituted aryl or $C_6$ to $C_{25}$ unsubstituted heteroaryl having one to three heteroatoms independently selected from the group consisting of O, N and S; and
(vi) $C_6$ to $C_{25}$ substituted aryl or $C_6$ to $C_{25}$ substituted heteroaryl having one to three heteroatoms independently selected from the group consisting of O, N and S;
and wherein said substituted aryl or substituted heteroaryl has one to three substituents independently selected from the group consisting of:
(1) —$CH_3$, —$C_2H_5$, or $C_3$ to $C_{25}$, preferably $C_3$ to $C_{20}$, straight-chain, branched or cyclic alkane or alkene, optionally substituted with at least one member selected from the group consisting of Cl, Br, F, I, OH, $NH_2$ and SH,
(2) OH,
(3) $NH_2$, and
(4) SH;
$R^7$, $R^8$, $R^9$, and $R^{10}$ are independently selected from the group consisting of:
(vii) —$CH_3$, —$C_2H_5$, or $C_3$ to $C_{25}$, preferably $C_3$ to $C_{20}$, straight-chain, branched or cyclic alkane or alkene, optionally substituted with at least one member selected from the group consisting of Cl, Br, F, I, OH, $NH_2$ and SH;
(viii) —$CH_3$, —$C_2H_5$, or $C_3$ to $C_{25}$, preferably $C_3$ to $C_{20}$, straight-chain, branched or cyclic alkane or alkene comprising one to three heteroatoms selected from the group consisting of O, N and S, and optionally substituted with at least one member selected from the group consisting of Cl, Br, F, I, OH, $NH_2$ and SH;
(ix) $C_6$ to $C_{25}$ unsubstituted aryl or $C_6$ to $C_{25}$ unsubstituted heteroaryl having one to three heteroatoms independently selected from the group consisting of O, N and S; and
(x) $C_6$ to $C_{25}$ substituted aryl or $C_6$ to $C_{25}$ substituted heteroaryl having one to three heteroatoms independently selected from the group consisting of O, N and S; and wherein said substituted aryl or substituted heteroaryl has one to three substituents independently selected from the group consisting of
(1) —$CH_3$, —$C_2H_5$, or $C_3$ to $C_{25}$, preferably $C_3$ to $C_{20}$, straight-chain, branched or cyclic alkane or alkene, optionally substituted with at least one member selected from the group consisting of Cl, Br, F, I, OH, $NH_2$ and SH,
(2) OH,
(3) $NH_2$, and
(4) SH; and wherein
optionally at least two of $R^1$, $R^2$, $R^3$, $R^4$, $R^5$, $R^6$, $R^7$, $R^8$, $R^9$, and $R^{10}$ can together form a cyclic or bicyclic alkanyl or alkenyl group;
and $A^-$ is an anion selected from the group consisting of Formulae I, II and III:

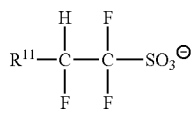

Formula I wherein:
$R^{11}$ is selected from the group consisting of:
(1) halogen;
(2) —$CH_3$, —$C_2H_5$ or $C_3$ to $C_{15}$, preferably $C_3$ to $C_6$, straight-chain or branched alkane or alkene, optionally substituted with at least one member selected from the group consisting of Cl, Br, I, OH, $NH_2$ and SH;
(3) —$OCH_3$, —$OC_2H_5$ or $C_3$ to $C_{15}$, preferably $C_3$ to $C_6$, straight-chain or branched alkoxy, optionally substituted with at least one member selected from the group consisting of Cl, Br, I, OH, $NH_2$ and SH;

(4) C₁ to C₁₅, preferably C₁ to C₆, straight-chain or branched fluoroalkyl, optionally substituted with at least one member selected from the group consisting of Cl, Br, I, OH, NH₂ and SH;
(5) C₁ to C₁₅, preferably C₁ to C₆, straight-chain or branched fluoroalkoxy, optionally substituted with at least one member selected from the group consisting of Cl, Br, I, OH, NH₂ and SH;
(6) C₁ to C₁₅, preferably C₁ to C₆, straight-chain or branched perfluoroalkyl; and
(7) C₁ to C₁₅, preferably C₁ to C₆, straight-chain or branched perfluoroalkoxy;

Formula II

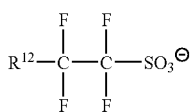

wherein:
R¹² is selected from the group consisting of:
(1) —OCH₃, —OC₂H₅ or C₃ to C₁₅, preferably C₃ to C₆, straight-chain or branched alkoxy, optionally substituted with at least one member selected from the group consisting of Cl, Br, I, OH, NH₂ and SH;
(2) C₁ to C₁₅, preferably C₁ to C₆, straight-chain or branched fluoroalkoxy, optionally substituted with at least one member selected from the group consisting of Cl, Br, I, OH, NH₂ and SH; and
(3) C₁ to C₁₅, preferably C₁ to C₆, straight-chain or branched perfluoroalkoxy; and Formula III

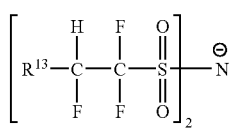

wherein:
R¹³ is selected from the group consisting of:
(1) halogen;
(2) —CH₃, —C₂H₅ or C₃ to C₁₅, preferably C₃ to C₆, straight-chain or branched alkane or alkene, optionally substituted with at least one member selected from the group consisting of Cl, Br, I, OH, NH₂ and SH;
(3) —OCH₃, —OC₂H₅ or C₃ to C₁₅, preferably C₃ to C₆, straight-chain or branched alkoxy, optionally substituted with at least one member selected from the group consisting of Cl, Br, I, OH, NH₂ and SH;
(4) C₁ to C₁₅, preferably C₁ to C₆, straight-chain or branched fluoroalkyl, optionally substituted with at least one member selected from the group consisting of Cl, Br, I, OH, NH₂ and SH;
(5) C₁ to C₁₅, preferably C₁ to C₆, straight-chain or branched fluoroalkoxy, optionally substituted with at least one member selected from the group consisting of Cl, Br, I, OH, NH₂ and SH;
(6) C₁ to C₁₅, preferably C₁ to C₆, straight-chain or branched perfluoroalkyl; and
(7) C₁ to C₁₅, preferably C₁ to C₆, straight-chain or branched perfluoroalkoxy.

In preferred embodiments of the invention, the anion is selected from the group consisting of 1,1,2,2-tetrafluoroethanesulfonate; 2-chloro-1,1,2-trifluoroethanesulfonate; 1,1,2,3,3,3-hexafluoropropanesulfonate; 1,1,2-trifluoro-2-(trifluoromethoxy)ethanesulfonate; 1,1,2-trifluoro-2-(pentafluoroethoxy)ethanesulfonate; 2-(1,2,2,2-tetrafluoroethoxy)-1,1,2,2-tetrafluoroethanesulfonate; 2-(1,1,2,2-tetrafluoroethoxy)-1,1,2,2-tetrafluoroethanesulfonate; 2-(1,1,2,2-tetrafluoro-2-iodoethoxy)-1,1,2,2-tetrafluoroethanesulfonate; 1,1,2,2-tetrafluoro-2-(pentafluoroethoxy)ethanesulfonate; N,N-bis(1,1,2,2-tetrafluoroethanesulfonyl)imide; and N,N-bis(1,1,2,3,3,3-hexafluoropropanesulfonyl)imide.

In one embodiment, the composition of the invention comprises a cation selected from the group consisting of pyridinium, pyridazinium, pyrimidinium, pyrazinium, imidazolium, pyrazolium, thiazolium, oxazolium, triazolium, phosphonium, ammonium as defined in all of the embodiments above; and said anion is selected from the group consisting of 1,1,2,2-tetrafluoroethanesulfonate; 2-chloro-1,1,2-trifluoroethanesulfonate; 1,1,2,3,3,3-hexafluoropropanesulfonate; 1,1,2-trifluoro-2-(trifluoromethoxy)ethanesulfonate; 1,1,2-trifluoro-2-(pentafluoroethoxy)ethanesulfonate; 2-(1,2,2,2-tetrafluoroethoxy)-1,1,2,2-tetrafluoroethanesulfonate; 2-(1,1,2,2-tetrafluoroethoxy)-1,1,2,2-tetrafluoroethanesulfonate; 2-(1,1,2,2-tetrafluoro-2-iodoethoxy)-1,1,2,2-tetrafluoroethanesulfonate; 1,1,2,2-tetrafluoro-2-(pentafluoroethoxy)ethanesulfonate; N,N-bis(1,1,2,2-tetrafluoroethanesulfonyl)imide; N,N-bis(1,1,2,3,3,3-hexafluoropropanesulfonyl)imide.

In another embodiment, the composition of the invention comprises 1-butyl-2,3-dimethylimidazolium 1,1,2,2-tetrafluoroethanesulfonate, 1-butyl-methylimidazolium 1,1,2,2-tetrafluoroethanesulfonate, 1-ethyl-3-methylimidazolium 1,1,2,2-tetrafluoroethanesulfonate, 1-ethyl-3-methylimidazolium 1,1,2,3,3,3-hexafluoropropanesulfonate, 1-hexyl-3-methylimidazolium 1,1,2,2-tetrafluoroethanesulfonate, 1-dodecyl-3-methylimidazolium 1,1,2,2-tetrafluoroethanesulfonate, 1-hexadecyl-3-methylimidazolium 1,1,2,2-tetrafluoroethanesulfonate, 1-octadecyl-3-methylimidazolium 1,1,2,2-tetrafluoroethanesulfonate, N-(1,1,2,2-tetrafluoroethyl)propylimidazole 1,1,2,2-tetrafluoroethanesulfonate, N-(1,1,2,2-tetrafluoroethyl)ethylperfluorohexylimidazole 1,1,2,2-tetrafluoroethanesulfonate, 1-butyl-3-methylimidazolium 1,1,2,3,3,3-hexafluoropropanesulfonate, 1-butyl-3-methylimidazolium 1,1,2-trifluoro-2-(trifluoromethoxy)ethanesulfonate, 1-butyl-3-methylimidazolium 1,1,2-trifluoro-2-(perfluoroethoxy)ethanesulfonate, tetradecyl(tri-n-hexyl)phosphonium 1,1,2-trifluoro-2-(perfluoroethoxy)ethanesulfonate, tetradecyl(tri-n-butyl)phosphonium 1,1,2,3,3,3-hexafluoropropanesulfonate, tetradecyl(tri-n-hexyl)phosphonium 1,1,2-trifluoro-2-(trifluoromethoxy)ethanesulfonate, 1-ethyl-3-methylimidazolium 1,1,2,2-tetrafluoro-2-(pentafluoroethoxy)sulfonate, (3,3,4,4,5,5,6,6,7,7,8,8,8-tridecafluorooctyl)-trioctylphosphonium 1,1,2,2-tetrafluoroethanesulfonate, 1-methyl-3-(3,3,4,4,5,5,6,6,7,7,8,8,8-tridecafluorooctyl)imidazolium 1,1,2,2-tetrafluoroethanesulfonate, or tetra-n-butylphosphonium 1,1,2-trifluoro-2-(perfluoroethoxy)ethanesulfonate.

Cations of the invention are available commercially, or may be synthesized by methods known to those skilled in the art. The fluoroalkyl sulfonate anions may be synthesized from perfluorinated terminal olefins or perfluorinated vinyl ethers generally according to the method of Koshar, et al. (J. Am. Chem. Soc. (1953) 75:4595-4596); in one embodiment, sulfite and bisulfite are used as the buffer in place of bisulfite and borax, and in another embodiment, the reaction is carried in the absence of a radical initiator. 1,1,2,2-Tetrafluoroethanesulfonate, 1,1,2,3,3,3-hexafluoropropanesulfonate, 1,1,2-trifluoro-2-(trifluoromethoxy)ethanesulfonate, and 1,1,2-trifluoro-2-(pentafluoroethoxy)ethanesulfonate may be synthesized according to Koshar, et al. (supra), with modifications. Preferred modifications include using a mixture of sulfite and bisulfite as the buffer, freeze drying or spray drying to isolate the crude 1,1,2,2-tetrafluoroethanesulfonate and 1,1,2,3,3,3-hexafluoropropanesulfonate products from the aqueous reaction mixture, using acetone to extract the crude 1,1,2,2-tetrafluoroethanesulfonate and 1,1,2,3,3,3-hexafluoropropanesulfonate salts, and crystallizing 1,1,2-trifluoro-2-(trifluoromethoxy)ethanesulfonate and 1,1,2-trifluoro-2-(pentafluoroethoxy)ethanesulfonate from the reaction mixture by cooling.

General Procedure for Synthesizing Ionic Liquids that are not Miscible with Water:

Solution #1 is made by dissolving a known amount of the halide salt of the cation in deionized water. This may involve heating to ensure total dissolution. Solution #2 is made by dissolving an approximately equimolar amount (relative to the cation) of the potassium or sodium salt of the anion in deionized water. This may also involve heating to ensure total dissolution. Although it is not necessary to use equimolar quantities of the cation and anion, a 1:1 equimolar ratio minimizes the impurities obtained by the reaction. The two aqueous solutions (#1 and #2) are mixed and stirred at a temperature that optimizes the separation of the desired product phase as either an oil or a solid on the bottom of the flask. In one embodiment, the aqueous solutions are mixed and stirred at room temperature, however the optimal temperature may be higher or lower based on the conditions necessary to achieve optimal product separation. The water layer is separated, and the product is washed several times with deionized water to remove chloride or bromide impurities. An additional base wash may help to remove acidic impurities. The product is then diluted with an appropriate organic solvent (chloroform, methylene chloride, etc.) and dried over anhydrous magnesium sulfate or other preferred drying agent. The appropriate organic solvent is one that is miscible with the ionic liquid and that can be dried. The drying agent is removed by suction filtration and the organic solvent is removed in vacuo. High vacuum is applied for several hours or until residual water is removed. The final product is usually in the form of a liquid.

General Procedure for the Synthesis of Ionic Liquids that are Miscible with Water:

Solution #1 is made by dissolving a known amount of the halide salt of the cation in an appropriate solvent. This may involve heating to ensure total dissolution. Preferably the solvent is one in which the cation and anion are miscible, and in which the salts formed by the reaction are minimally miscible; in addition, the appropriate solvent is preferably one that has a relatively low boiling point such that the solvent can be easily removed after the reaction. Appropriate solvents include, but are not limited to, high purity dry acetone, alcohols such as methanol and ethanol, and acetonitrile. Solution #2 is made by dissolving an equimolar amount (relative to the cation) of the salt (generally potassium or sodium) of the anion in an appropriate solvent, typically the same as that used for the cation. This may also involve heating to ensure total dissolution. The two solutions (#1 and #2) are mixed and stirred under conditions that result in approximately complete precipitation of the halide salt byproduct (generally potassium halide or sodium halide); in one embodiment of the invention, the solutions are mixed and stirred at approximately room temperature for about 4-12 hours. The halide salt is removed by suction filtration through an acetone/celite pad, and color can be reduced through the use of decolorizing carbon as is known to those skilled in the art. The solvent is removed in vacuo and then high vacuum is applied for several hours or until residual water is removed. The final product is usually in the form of a liquid.

Compositions (ionic liquids) of the present invention can be utilized in one phase systems or multiple phase systems as solvents or, perhaps, as catalysts. The physical and chemical properties of the compositions of the present invention can be specifically selected by choice of the appropriate cation and anion. For example, increasing the chain length of one or more alkyl chains of the cation will affect properties such as the melting point, hydrophilicity/lipophilicity, density and salvation strength of the ionic liquid. Choice of the anion can affect, for example, the melting point, the water solubility and the acidity and coordination properties of the composition. Effects of cation and anion on the physical and chemical properties of ionic liquids are known to those skilled in the art and are reviewed in detail by Wasserscheid and Keim (Angew. Chem. Int. Ed. (2000) 39:3772-3789) and Sheldon (Chem. Commun. (2001) 2399-2407).

Preparation of Polytrimethylene Ether Glycol

Compositions of the present invention are useful for the polymerization of 1,3-propanediol. To prepare polytrimethylene ether glycol, 1,3-propanediol is contacted with at least one polycondensation catalyst and at least one ionic liquid of the invention to form a polyether phase comprising polytrimethylene ether glycol and an ionic liquid phase. The polyether phase is then separated from the ionic liquid phase.

The 1,3-propanediol may be obtained commercially or by any of the various chemical routes or by biochemical transformation routes well known to those skilled in the art.

The temperature of the process is preferably controlled to achieve high yields of desired molecular weight and a minimum of color formation. The polycondensation reaction is preferably carried out at a temperature of from about 120 degrees C. to about 250 degrees C. In one embodiment, the temperature is from about 120 degrees C. to about 210 degrees C.; in another embodiment the temperature is from about 120 degrees C. to about 180 degrees C.; in still another embodiment, the temperature is from about 140 degrees C. to about 180 degrees C.

The polycondensation may be carried out under an inert atmosphere, such as nitrogen or argon. In another embodiment, the polycondensation is carried out at a pressure of less than about 100 KPa; in additional embodiments the reaction is carried out at a pressure of less than about 67 KPa, preferably less than about 33 KPa.

The time for the reaction will depend on many factors, such as the reactants, reaction conditions and reactor. One skilled in the art will know to adjust the time for the reaction to achieve high yields of polytrimethylene ether glycol (or copolymers thereof) of the desired molecular weight.

The at least one polycondensation catalyst is a homogeneous acid catalyst. In one embodiment of the invention, suitable homogeneous acid catalysts are those having a pKa of less than about 4; in another embodiment, suitable homogeneous acid catalysts are those having a pKa of less than about 2.

In one embodiment, the at least one polycondensation catalyst is a homogeneous acid catalyst selected from the group consisting of inorganic acids, organic sulfonic acids, heteropolyacids, fluoroalkyl sulfonic acids, metal sulfonates, metal trifluoroacetates, compounds thereof and combinations thereof. In yet another embodiment, the at least one polycondensation catalyst is a homogeneous acid catalyst selected from the group consisting of sulfuric acid, fluorosulfonic acid, phosphorous acid, p-toluenesulfonic acid, benzenesulfonic acid, phosphotungstic acid, phosphomolybdic acid, trifluoromethanesulfonic acid, nonafluorobutanesulfonic acid, 1,1,2,2-tetrafluoroethanesulfonic acid, 1,1,2,3,3,3-hexafluoropropanesulfonic acid, bismuth triflate, yttrium triflate, ytterbium triflate, neodymium triflate, lanthanum triflate, scandium triflate, and zirconium triflate. The catalyst is used at a concentration of from about 0.1% to about 20% by weight of the 1,3-propanediol reactant.

The polycondensation reaction may be carried out as a batch or continuous process. Reactor configurations, as well as a continuous process for polycondensation of 1,3-propanediol reactant, are described in U.S. Pat. No. 6,720,459, Column 5, line 49 through Column 9, line 26, and FIGS. 1 through 6.

An advantage to the use of at least one ionic liquid in this reaction is that the reaction product comprises a polyether phase comprising polytrimethylene ether glycol and an ionic liquid phase that comprises the acid catalyst. Thus the polytrimethylene ether glycol product or products in the polyether phase is/are easily recoverable from the acid catalyst by, for example, decantation. In a preferred embodiment, the acid catalyst and the at least one ionic liquid are recycled and used in subsequent reactions.

General Materials and Methods

The following abbreviations are used:

Nuclear magnetic resonance is abbreviated NMR; gas chromatography is abbreviated GC; gas chromatography-mass spectrometry is abbreviated GC-MS; thin layer chromatography is abbreviated TLC; thermogravimetric analysis (using a Universal V3.9A TA instrument analyzer (TA Instruments, Inc., Newcastle, Del.)) is abbreviated TGA. Centigrade is abbreviated C, mega Pascal is abbreviated MPa, gram is abbreviated g, kilogram is abbreviated Kg, milliliter(s) is abbreviated ml(s), hour is abbreviated hr; weight percent is abbreviated wt %; milliequivalents is abbreviated meq; melting point is abbreviated Mp; differential scanning calorimetry is abbreviated DSC.

1-Butyl-2,3-dimethylimidazolium chloride, 1-hexyl-3-methylimidazolium chloride, 1-dodecyl-3-methylimidazolium chloride, 1-hexadecyl-3-methyl imidazolium chloride, 1-octadecyl-3-methylimidazolium chloride, imidazole, tetrahydrofuran, iodopropane, acetonitrile, iodoperfluorohexane, toluene, 1,3-propanediol, oleum (20% $SO_3$), sodium sulfite ($Na_2SO_3$, 98%), and acetone were obtained from Acros (Hampton, N.H.). Potassium metabisulfite ($K_2S_2O_5$, 99%), was obtained from Mallinckrodt Laboratory Chemicals (Phillipsburg, N.J.). Potassium sulfite hydrate ($KHSO_3$.$xH_2O$, 95%), sodium bisulfite ($NaHSO_3$), sodium carbonate, magnesium sulfate, ethyl ether, 1,1,1,2,2,3,3,4,4,5,5,6,6-tridecafluoro-8-iodooctane, trioctyl phosphine and 1-ethyl-3-methylimidazolium chloride (98%) were obtained from Aldrich (St. Louis, Mo.). Sulfuric acid and methylene chloride were obtained from EMD Chemicals, Inc. (Gibbstown, N.J.). Perfluoro(ethylvinyl ether), perfluoro(methylvinyl ether), hexafluoropropene and tetrafluoroethylene were obtained from DuPont Fluoroproducts (Wilmington, Del.). 1-Butyl-methylimidazolium chloride was obtained from Fluka (Sigma-Aldrich, St. Louis, Mo.). Tetra-n-butylphosphonium bromide and tetradecyl(tri-n-hexyl)phosphonium chloride were obtained from Cytec (Canada Inc., Niagara Falls, Ontario, Canada). 1,1,2,2-Tetrafluoro-2-(pentafluoroethoxy)sulfonate was obtained from SynQuest Laboratories, Inc. (Alachua, Fla.).

Preparation of Formula I Anions not Generally Available Commercially (A) Synthesis of Potassium 1,1,2,2-tetrafluoroethanesulfonate (TFES-K) ($[HCF_2CF_2SO_3]^-$)

A 1-gallon Hastelloy® C276 reaction vessel was charged with a solution of potassium sulfite hydrate (176 g, 1.0 mol), potassium metabisulfite (610 g, 2.8 mol) and deionized water (2000 ml). The pH of this solution was 5.8. The vessel was cooled to 18 degrees C., evacuated to 0.10 MPa, and purged with nitrogen. The evacuate/purge cycle was repeated two more times. To the vessel was then added tetrafluoroethylene (TFE, 66 g), and it was heated to 100 degrees C. at which time the inside pressure was 1.14 MPa. The reaction temperature was increased to 125 degrees C. and kept there for 3 hr. As the TFE pressure decreased due to the reaction, more TFE was added in small aliquots (20-30 g each) to maintain operating pressure roughly between 1.14 and 1.48 MPa. Once 500 g (5.0 mol) of TFE had been fed after the initial 66 g precharge, the vessel was vented and cooled to 25 degrees C. The pH of the clear light yellow reaction solution was 10-11. This solution was buffered to pH 7 through the addition of potassium metabisulfite (16 g).

The water was removed in vacuo on a rotary evaporator to produce a wet solid. The solid was then placed in a freeze dryer (Virtis Freezemobile 35xl; Gardiner, N.Y.) for 72 hr to reduce the water content to approximately 1.5 wt % (1387 g crude material). The theoretical mass of total solids was 1351 g. The mass balance was very close to ideal and the isolated solid had slightly higher mass due to moisture. This added freeze drying step had the advantage of producing a free-flowing white powder whereas treatment in a vacuum oven resulted in a soapy solid cake that was very difficult to remove and had to be chipped and broken out of the flask.

The crude TFES-K can be further purified and isolated by extraction with reagent grade acetone, filtration, and drying.

$^{19}F$ NMR ($D_2O$) δ −122.0 (dt, $J_{FH}$=6 Hz, $J_{FF}$=6 Hz, 2F); −136.1 (dt, $J_{FH}$=53 Hz, 2F).

$^1H$ NMR ($D_2O$) δ 6.4 (tt, $J_{FH}$=53 Hz, $J_{FH}$=6 Hz, 1H).

% Water by Karl-Fisher titration: 580 ppm.

Analytical calculation for $C_2HO_3F_4SK$: C, 10.9; H, 0.5; N, 0.0

Experimental results: C, 11.1; H, 0.7; N, 0.2.

Mp (DSC): 242 degrees C.

TGA (air): 10% wt. loss @ 367 degrees C., 50% wt. loss @ 375 degrees C.

TGA ($N_2$): 10% wt. loss @ 363 degrees C., 50% wt. loss @ 375 degrees C.

(B) Synthesis of potassium-1,1,2-trifluoro-2-(perfluoroethoxy)ethanesulfonate (TPES-K)

A 1-gallon Hastelloy® C276 reaction vessel was charged with a solution of potassium sulfite hydrate (88 g, 0.56 mol), potassium metabisulfite (340 g, 1.53 mol) and deionized water (2000 ml). The vessel was cooled to 7 degrees C., evacuated to 0.05 MPa, and purged with nitrogen. The evacuate/purge cycle was repeated two more times. To the vessel was then added perfluoro(ethylvinyl ether) (PEVE, 600 g, 2.78 mol), and it was heated to 125 degrees C. at which time the inside pressure was 2.31 MPa. The reaction temperature was maintained at 125 degrees C. for 10 hr. The pressure dropped to 0.26 MPa at which point the vessel was vented and cooled to 25 degrees C.

The crude reaction product was a white crystalline precipitate with a colorless aqueous layer (pH=7) above it.

The $^{19}$F NMR spectrum of the white solid showed pure desired product, while the spectrum of the aqueous layer showed a small but detectable amount of a fluorinated impurity. The desired isomer is less soluble in water so it precipitated in isomerically pure form.

The product slurry was suction filtered through a fritted glass funnel, and the wet cake was dried in a vacuum oven (60 degrees C., 0.01 MPa) for 48 hr. The product was obtained as off-white crystals (904 g, 97% yield).

$^{19}$F NMR (D$_2$O) δ −86.5 (s, 3F); −89.2, −91.3 (subsplit ABq, J$_{FF}$=147 Hz, 2F);
−119.3, −121.2 (subsplit ABq, J$_{FF}$=258 Hz, 2F); −144.3 (dm, J$_{FH}$=53 Hz, 1F).

$^1$H NMR (D$_2$O) δ 6.7 (dm, J$_{FH}$=53 Hz, 1H).

Mp (DSC) 263 degrees C.

Analytical calculation for C$_4$HO$_4$F$_8$SK: C, 14.3; H, 0.3. Experimental results: C, 14.1; H, 0.3.

TGA (air): 10% wt. loss @ 359 degrees C., 50% wt. loss @ 367 degrees C.

TGA (N$_2$): 10% wt. loss @ 362 degrees C., 50% wt. loss @ 374 degrees C.

(C) Synthesis of potassium-1,1,2-trifluoro-2-(trifluoromethoxy)ethanesulfonate (TTES-K)

A 1-gallon Hastelloy® C276 reaction vessel was charged with a solution of potassium sulfite hydrate (114 g, 0.72 mol), potassium metabisulfite (440 g, 1.98 mol) and deionized water (2000 ml). The pH of this solution was 5.8. The vessel was cooled to −35 degrees C., evacuated to 0.08 MPa, and purged with nitrogen. The evacuate/purge cycle was repeated two more times. To the vessel was then added perfluoro(methylvinyl ether) (PMVE, 600 g, 3.61 mol) and it was heated to 125 degrees C. at which time the inside pressure was 3.29 MPa. The reaction temperature was maintained at 125 degrees C. for 6 hr. The pressure dropped to 0.27 MPa at which point the vessel was vented and cooled to 25 degrees C. Once cooled, a white crystalline precipitate of the desired product formed leaving a colorless clear aqueous solution above it (pH=7).

The $^{19}$F NMR spectrum of the white solid showed pure desired product, while the spectrum of the aqueous layer showed a small but detectable amount of a fluorinated impurity.

The solution was suction filtered through a fritted glass funnel for 6 hr to remove most of the water. The wet cake was then dried in a vacuum oven at 0.01 MPa and 50 degrees C. for 48 hr. This gave 854 g (83% yield) of a white powder. The final product was isomerically pure (by $^{19}$F and $^1$H NMR) since the undesired isomer remained in the water during filtration.

$^{19}$F NMR (D$_2$O) δ −59.9 (d, J$_{FH}$=4 Hz, 3F); −119.6, −120.2 (subsplit ABq, J=260 Hz, 2F); −144.9 (dm, J$_{FH}$=53 Hz, 1F).

$^1$H NMR (D$_2$O) δ 6.6 (dm, J$_{FH}$=53 Hz, 1H).

% Water by Karl-Fisher titration: 71 ppm.

Analytical calculation for C$_3$HF$_6$SO$_4$K: C, 12.6; H, 0.4; N, 0.0.

Experimental results: C, 12.6; H, 0.0; N, 0.1.

Mp (DSC) 257 degrees C.

TGA (air): 10% wt. loss @ 343 degrees C., 50% wt. loss @ 358 degrees C.

TGA (N$_2$): 10% wt. loss @ 341 degrees C., 50% wt. loss @ 357 degrees C.

(D) Synthesis of sodium 1,1,2,3,3,3-hexafluoropropanesulfonate (HFPS-Na)

A 1-gallon Hastelloy® C reaction vessel was charged with a solution of anhydrous sodium sulfite (25 g, 0.20 mol), sodium bisulfite 73 g, (0.70 mol) and of deionized water (400 ml). The pH of this solution was 5.7. The vessel was cooled to 4 degrees C., evacuated to 0.08 MPa, and then charged with hexafluoropropene (HFP, 120 g, 0.8 mol, 0.43 MPa). The vessel was heated with agitation to 120 degrees C. and kept there for 3 hr. The pressure rose to a maximum of 1.83 MPa and then dropped down to 0.27 MPa within 30 minutes. At the end, the vessel was cooled and the remaining HFP was vented, and the reactor was purged with nitrogen. The final solution had a pH of 7.3.

The water was removed in vacuo on a rotary evaporator to produce a wet solid. The solid was then placed in a vacuum oven (0.02 MPa, 140 degrees C., 48 hr) to produce 219 g of white solid which contained approximately 1 wt % water. The theoretical mass of total solids was 217 g.

The crude HFPS-Na can be further purified and isolated by extraction with reagent grade acetone, filtration, and drying.

$^{19}$F NMR (D$_2$O) δ −74.5 (m, 3F); −113.1, −120.4 (ABq, J=264 Hz, 2F); −211.6 (dm, 1F).

$^1$H NMR (D$_2$O) δ 5.8 (dm, J$_{FH}$=43 Hz, 1H).

Mp (DSC) 126 degrees C.

TGA (air): 10% wt. loss @ 326 degrees C., 50% wt. loss @ 446 degrees C.

TGA (N$_2$): 10% wt. loss @ 322 degrees C., 50% wt. loss @ 449 degrees C.

Examples 1-19 exemplify the synthesis of compositions of the invention.

EXAMPLE 1

Synthesis of 1-butyl-2,3-dimethylimidazolium 1,1,2,2-tetrafluoroethanesulfonate (Cation, imidazolium; Anion, Formula 1)

1-Butyl-2,3-dimethylimidazolium chloride (22.8 g, 0.121 moles) was mixed with reagent-grade acetone (250 ml) in a large round-bottomed flask and stirred vigorously. Potassium 1,1,2,2-tetrafluoroethanesulfonate (TFES-K, 26.6 g, 0.121 moles) was added to reagent grade acetone (250 ml) in a separate round-bottomed flask, and this solution was carefully added to the 1-butyl-2,3-dimethylimidazolium chloride solution. The large flask was lowered into an oil bath and heated at 60 degrees C. under reflux for 10 hours. The reaction mixture was then filtered using a large frit glass funnel to remove the white KCl precipitate formed, and the filtrate was placed on a rotary evaporator for 4 hours to remove the acetone. The product was isolated and dried under vacuum at 150 degrees C. for 2 days.

$^1$H NMR (DMSO-d$_6$): δ 0.9 (t, 3H); 1.3 (m, 2H); 1.7 (m, 2H); 2.6 (s, 3H); 3.8 (s, 3H); 4.1 (t, 2H); 6.4 (tt, 1H); 7.58 (s, 1H); 7.62 (s, 1H).

% Water by Karl-Fischer titration: 0.06%.

TGA (air): 10% wt. loss @ 375 degrees C., 50% wt. loss @ 415 degrees C.

TGA (N$_2$): 10% wt. loss @ 395 degrees C., 50% wt. loss @ 425 degrees C.

The reaction scheme is shown below:

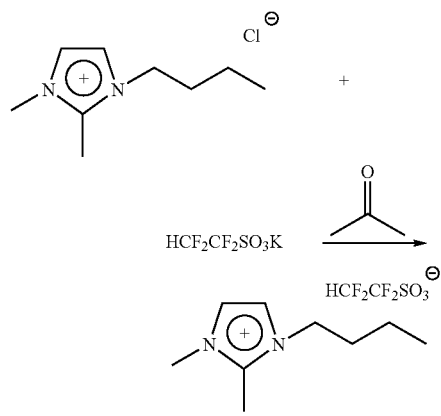

EXAMPLE 2

Synthesis of 1-butyl-3-methylimidazolium
1,1,2,2-tetrafluoroethanesulfonate (Bmim-TFES)
(Cation, imidazolium; Anion, Formula 1)

1-Butyl-3-methylimidazolium chloride (60.0 g) and high purity dry acetone (>99.5%, 300 ml) were combined in a 1 liter flask and warmed to reflux with magnetic stirring until the solid completely dissolved. At room temperature in a separate 1 liter flask, potassium-1,1,2,2-tetrafluoroethane-sulfonte (TFES-K, 75.6 g) was dissolved in high purity dry acetone (500 ml). These two solutions were combined at room temperature and allowed to stir magnetically for 2 hr under positive nitrogen pressure. The stirring was stopped and the KCl precipitate was allowed to settle, then removed by suction filtration through a fritted glass funnel with a celite pad. The acetone was removed in vacuo to give a yellow oil. The oil was further purified by diluting with high purity acetone (100 ml) and stirring with decolorizing carbon (5 g). The mixture was again suction filtered and the acetone removed in vacuo to give a colorless oil. This was further dried at 4 Pa and 25 degrees C. for 6 hr to provide 83.6 g of product.

$^{19}$F NMR (DMSO-d$_6$) δ −124.7 (dt, J=6 Hz, J=8 Hz, 2F); −136.8 (dt, J=53 Hz, 2F).

$^1$H NMR (DMSO-d$_6$) δ 0.9 (t, J=7.4 Hz, 3H); 1.3 (m, 2H); 1.8 (m, 2H); 3.9 (s, 3H); 4.2 (t, J=7 Hz, 2H); 6.3 (dt, J=53 Hz, J=6 Hz, 1H); 7.4 (s, 1H); 7.5 (s, 1H); 8.7 (s, 1H).

% Water by Karl-Fisher titration: 0.14%.

Analytical calculation for C$_9$H$_{12}$F$_6$N$_2$O$_3$S: C, 37.6; H, 4.7; N, 8.8.

Experimental Results: C, 37.6; H, 4.6; N, 8.7.

TGA (air): 10% wt. loss @ 380 degrees C., 50% wt. loss @ 420 degrees C.

TGA (N$_2$): 10% wt. loss @ 375 degrees C., 50% wt. loss @ 422 degrees C.

EXAMPLE 3

Synthesis of 1-ethyl-3-methylimidazolium
1,1,2,2-tetrafluoroethanesulfonate (Emim-TFES)
(Cation, imidazolium; Anion, Formula 1)

To a 500 ml round bottom flask was added 1-ethyl-3-methylimidazolium chloride (Emim-Cl, 98%, 61.0 g) and reagent grade acetone (500 ml). The mixture was gently warmed (50 degrees C.) until almost all of the Emim-Cl dissolved. To a separate 500 ml flask was added potassium 1,1,2,2-tetrafluoroethanesulfonate (TFES-K, 90.2 g) along with reagent grade acetone (350 ml). This second mixture was stirred magnetically at 24 degrees C. until all of the TFES-K dissolved.

These solutions were combined in a 1 liter flask producing a milky white suspension. The mixture was stirred at 24 degrees C. for 24 hrs. The KCl precipitate was then allowed to settle leaving a clear green solution above it.

The reaction mixture was filtered once through a celite/acetone pad and again through a fritted glass funnel to remove the KCl. The acetone was removed in vacuo first on a rotovap and then on a high vacuum line (4 Pa, 25 degrees C.) for 2 hr. The product was a viscous light yellow oil (76.0 g, 64% yield).

$^{19}$F NMR (DMSO-d$_6$) δ −124.7 (dt, J$_{FH}$=6 Hz, J$_{FF}$=6 Hz, 2F); −138.4 (dt, J$_{FH}$=53 Hz, 2F).

$^1$H NMR (DMSO-d$_6$) δ 1.3 (t, J=7.3 Hz, 3H); 3.7 (s, 3H); 4.0 (q, J=7.3 Hz, 2H);

6.1 (tt, J$_{FH}$=53 Hz, J$_{FH}$=6 Hz, 1H); 7.2 (s, 1H); 7.3 (s, 1H); 8.5 (s, 1H).

% Water by Karl-Fisher titration: 0.18%.

Analytical calculation for C$_8$H$_{12}$N$_2$O$_3$F$_4$S: C, 32.9; H, 4.1; N, 9.6. Found: C, 33.3; H, 3.7; N, 9.6.

Mp 45-46 degrees C.

TGA (air): 10% wt. loss @ 379 degrees C., 50% wt. loss @ 420 degrees C.

TGA (N$_2$): 10% wt. loss @ 378 degrees C., 50% wt. loss @ 418 degrees C.

The reaction scheme is shown below:

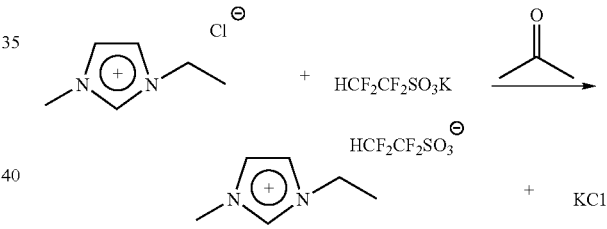

EXAMPLE 4

Synthesis of 1-ethyl-3-methylimidazolium
1,1,2,3,3,3-hexafluoropropanesulfonate
(Emim-HFPS) (Cation, imidazolium; Anion,
Formula 1)

To a 1 l round bottom flask was added 1-ethyl-3-methylimidazolium chloride (Emim-Cl, 98%, 50.5 g) and reagent grade acetone (400 ml). The mixture was gently warmed (50 degrees C.) until almost all of the Emim-Cl dissolved. To a separate 500 ml flask was added potassium 1,1,2,3,3,3-hexafluoropropanesulfonate (HFPS-K, 92.2 g) along with reagent grade acetone (300 ml). This second mixture was stirred magnetically at room temperature until all of the HFPS-K dissolved.

These solutions were combined and stirred under positive N$_2$ pressure at 26 degrees C. for 12 hr producing a milky white suspension. The KCl precipitate was allowed to settle overnight leaving a clear yellow solution above it.

The reaction mixture was filtered once through a celite/acetone pad and again through a fritted glass funnel. The acetone was removed in vacuo first on a rotovap and then on a high vacuum line (4 Pa, 25 degrees C.) for 2 hr. The product was a viscous light yellow oil (103.8 g, 89% yield).

$^{19}$F NMR (DMSO-d$_6$) δ −73.8 (s, 3F); −114.5, −121.0 (ABq, J=258 Hz, 2F); −210.6 (m, 1F, J$_{HF}$=41.5 Hz).

$^1$H NMR (DMSO-d$_6$) δ 1.4 (t, J=7.3 Hz, 3H); 3.9 (s, 3H); 4.2 (q, J=7.3 Hz, 2H,); 5.8 (m, J$_{HF}$=41.5 Hz, 1H,); 7.7 (s, 1H); 7.8 (s, 1H); 9.1 (s, 1H).

% Water by Karl-Fisher titration: 0.12%.

Analytical calculation for C$_9$H$_{12}$N$_2$O$_3$F$_6$S: C, 31.5; H, 3.5; N, 8.2.

Experimental Results: C, 30.9; H, 3.3; N, 7.8.

TGA (air): 10% wt. loss @ 342 degrees C., 50% wt. loss @ 373 degrees C.

TGA (N$_2$): 10% wt. loss @ 341 degrees C., 50% wt. loss @ 374 degrees C.

The reaction scheme is shown below:

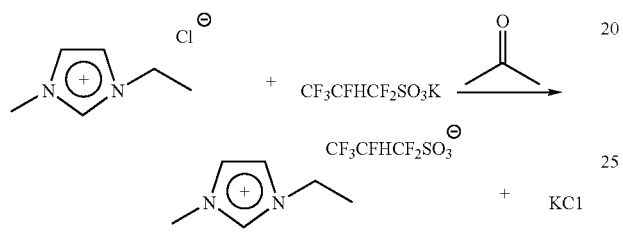

EXAMPLE 5

Synthesis of 1-hexyl-3-methylimidazolium 1,1,2,2-tetrafluoroethanesulfonate (Cation, imidazolium; Anion, Formula 1)

1-Hexyl-3-methylimidazolium chloride (10 g, 0.0493 moles) was mixed with reagent-grade acetone (100 ml) in a large round-bottomed flask and stirred vigorously under a nitrogen blanket. Potassium 1,1,2,2-tetrafluoroethane sulfonate (TFES-K, 10 g, 0.0455 moles) was added to reagent grade acetone (100 ml) in a separate round-bottomed flask, and this solution was carefully added to the 1-hexyl-3-methylimidazolium chloride/acetone mixture. The mixture was left to stir overnight. The reaction mixture was then filtered using a large frit glass funnel to remove the white KCl precipitate formed, and the filtrate was placed on a rotary evaporator for 4 hours to remove the acetone.

Appearance: pale yellow, viscous liquid at room temperature.

$^1$H NMR (DMSO-d$_6$): δ 0.9 (t, 3H); 1.3 (m, 6H); 1.8 (m, 2H); 3.9 (s, 3H); 4.2 (t, 2H); 6.4 (tt, 1H); 7.7 (s, 1H); 7.8 (s, 1H); 9.1 (s, 1H).

% Water by Karl-Fisher titration: 0.03%

TGA (air): 10% wt. loss @ 365 degrees C., 50% wt. loss @ 410 degrees C.

TGA (N$_2$): 10% wt. loss @ 370 degrees C., 50% wt. loss @ 415 degrees C.

The reaction scheme is shown below:

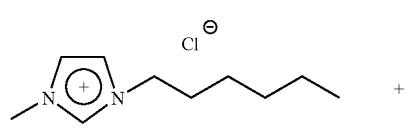

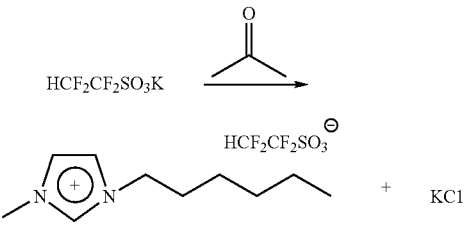

EXAMPLE 6

Synthesis of 1-dodecyl-3-methylimidazolium 1,1,2,2-tetrafluoroethanesulfonate (Cation, imidazolium; Anion, Formula 1)

1-Dodecyl-3-methylimidazolium chloride (34.16 g, 0.119 moles) was partially dissolved in reagent-grade acetone (400 ml) in a large round-bottomed flask and stirred vigorously. Potassium 1,1,2,2-tetrafluoroethanesulfonate (TFES-K, 26.24 g, 0.119 moles) was added to reagent grade acetone (400 ml) in a separate round-bottomed flask, and this solution was carefully added to the 1-dodecyl-3-methylimidazolium chloride solution. The reaction mixture was heated at 60 degrees C. under reflux for approximately 16 hours. The reaction mixture was then filtered using a large frit glass funnel to remove the white KCl precipitate formed, and the filtrate was placed on a rotary evaporator for 4 hours to remove the acetone.

$^1$H NMR (CD$_3$CN): δ 0.9 (t, 3H); 1.3 (m. 18H); 1.8 (m, 2H); 3.9 (s, 3H); 4.2 (t, 2H); 6.4 (tt, 1H); 7.7 (s, 1H); 7.8 (s, 1H); 9.1 (s, 1H).

$^{19}$F NMR (CD$_3$CN): δ −125.3 (m, 2F); −137 (dt, 2F).

% Water by Karl-Fischer titration: 0.24%

TGA (air): 10% wt. loss @ 370 degrees C., 50% wt. loss @ 410 degrees C.

TGA (N$_2$): 10% wt. loss @ 375 degrees C., 50% wt. loss @ 410 degrees C.

The reaction scheme is shown below:

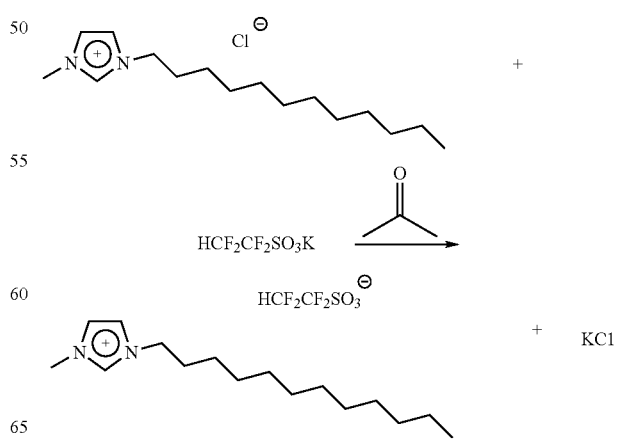

EXAMPLE 7

Synthesis of 1-hexadecyl-3-methylimidazolium 1,1,2,2-tetrafluoroethanesulfonate (Cation, imidazolium; Anion, Formula 1)

1-Hexadecyl-3-methylimidazolium chloride (17.0 g, 0.0496 moles) was partially dissolved in reagent-grade acetone (100 ml) in a large round-bottomed flask and stirred vigorously. Potassium 1,1,2,2-tetrafluoroethanesulfonate (TFES-K, 10.9 g, 0.0495 moles) was added to reagent grade acetone (100 ml) in a separate round-bottomed flask, and this solution was carefully added to the 1-hexadecyl-3-methylimidazolium chloride solution. The reaction mixture was heated at 60 degrees C. under reflux for approximately 16 hours. The reaction mixture was then filtered using a large frit glass funnel to remove the white KCl precipitate formed, and the filtrate was placed on a rotary evaporator for 4 hours to remove the acetone.

Appearance: white solid at room temperature.
$^1$H NMR (CD$_3$CN): δ 0.9 (t, 3H); 1.3 (m, 26H); 1.9 (m, 2H); 3.9 (s, 3H); 4.2 (t, 2H); 6.3 (tt, 1H); 7.4 (s, 1H); 7.4 (s, 1H); 8.6 (s, 1H).
$^{19}$F NMR (CD$_3$CN): δ −125.2 (m, 2F); −136.9 (dt, 2F).
% Water by Karl-Fischer titration: 200 ppm.
TGA (air): 10% wt. loss @ 360 degrees C., 50% wt. loss @ 395 degrees C.
TGA (N$_2$): 10% wt. loss @ 370 degrees C., 50% wt. loss @ 400 degrees C.

The reaction scheme is shown below:

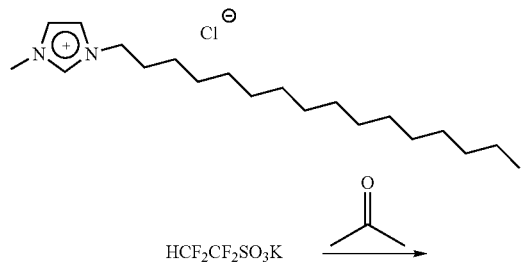

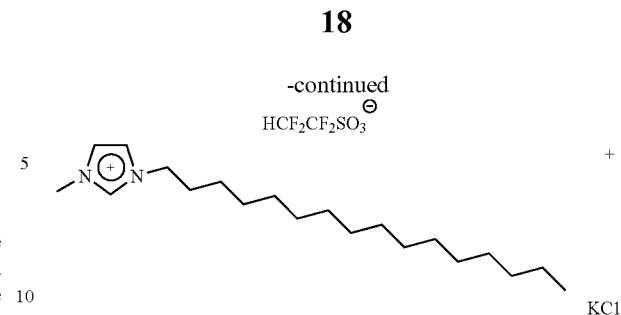

EXAMPLE 8

Synthesis of 1-octadecyl-3-methylimidazolium 1,1,2,2-tetrafluoroethanesulfonate (Cation, imidazolium; Anion, Formula 1)

1-Octadecyl-3-methylimidazolium chloride (17.0 g, 0.0458 moles) was partially dissolved in reagent-grade acetone (200 ml) in a large round-bottomed flask and stirred vigorously. Potassium 1,1,2,2-tetrafluoroethanesulfonate (TFES-K, 10.1 g, 0.0459 moles), was added to reagent grade acetone (200 ml) in a separate round-bottomed flask, and this solution was carefully added to the 1-octadecyl-3-methylimidazolium chloride solution. The reaction mixture was heated at 60 degrees C. under reflux for approximately 16 hours. The reaction mixture was then filtered using a large frit glass funnel to remove the white KCl precipitate formed, and the filtrate was placed on a rotary evaporator for 4 hours to remove the acetone.

$^1$H NMR (CD$_3$CN): δ 0.9 (t, 3H); 1.3 (m, 30H); 1.9 (m, 2H); 3.9 (s, 3H); 4.1 (t, 2H); 6.3 (tt, 1H); 7.4 (s, 1H); 7.4 (s, 1H); 8.5 (s, 1H).
$^{19}$F NMR (CD$_3$CN): δ −125.3 (m, 2F); −136.9 (dt, 2F).
% Water by Karl-Fischer titration: 0.03%.
TGA (air): 10% wt. loss @ 360 degrees C., 50% wt. loss @ 400 degrees C.
TGA (N$_2$): 10% wt. loss @ 365 degrees C., 50% wt. loss @ 405 degrees C.

The reaction scheme is shown below:

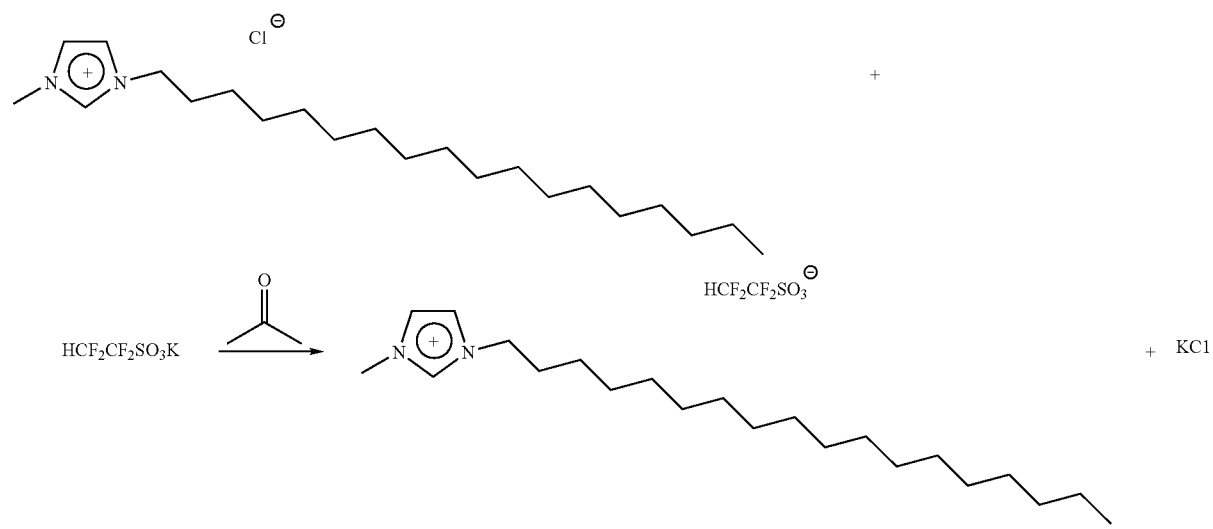

EXAMPLE 9

Synthesis of 1-propyl-3-(1,1,2,2-TFES) imidazolium 1,1,2,2-tetrafluoroethanesulfonate (Cation, imidazolium; Anion, Formula 1)

Imidazole (19.2 g) was added to of tetrahydrofuran (80 mls). A glass shaker tube reaction vessel was filled with the THF-containing imidazole solution. The vessel was cooled to 18° C., evacuated to 0.08 MPa, and purged with nitrogen. The evacuate/purge cycle was repeated two more times. Tetrafluoroethylene (TFE, 5 g) was then added to the vessel, and it was heated to 100 degrees C., at which time the inside pressure was about 0.72 MPa. As the TFE pressure decreased due to the reaction, more TFE was added in small aliquots (5 g each) to maintain operating pressure roughly between 0.34 MPa and 0.86 MPa. Once 40 g of TFE had been fed, the vessel was vented and cooled to 25 degrees C. The THF was then removed under vacuum and the product was vacuum distilled at 40 degrees C. to yield pure product as shown by $^1H$ and $^{19}F$ NMR (yield 44 g). Iodopropane (16.99 g) was mixed with 1-(1,1,2,2-tetrafluoroethyl)imidazole (16.8 g) in dry acetonitrile (100 ml), and the mixture was refluxed for 3 days. The solvent was removed in vacuo, yielding a yellow waxy solid (yield 29 g). The product, 1-propyl-3-(1,1,2,2-tetrafluoroethyl)imidazolium iodide was confirmed by $^1H$ NMR (in $CD_3CN$) [0.96 (t, 3H); 1.99 (m, 2H); 4.27 (t, 2H); 6.75 (t, 1H); 7.72 (d, 2H); 9.95 (s, 1H)].

Iodide (24 g) was then added to 60 ml of dry acetone, followed by 15.4 g of potassium 1,1,2,2-tetrafluoroethanesulfonate in 75 ml of dry acetone. The mixture was heated at 60 degrees C. overnight and a dense white precipitate was formed (potassium iodide). The mixture was cooled, filtered, and the solvent from the filtrate was removed using a rotary evaporator. Some further potassium iodide was removed under filtration. The product was further purified by adding 50 g of acetone, 1 g of charcoal, 1 g of celite and 1 g of silica gel. The mixture was stirred for 2 hours, filtered and the solvent removed. This yielded 15 g of a liquid, shown by NMR to be the desired product.

EXAMPLE 10

Synthesis of 1-butyl-3-methylimidazolium 1,1,2,3,3,3-hexafluoropropanesulfonate (Bmim-HFPS) (Cation, imidazolium; Anion, Formula 1)

1-Butyl-3-methylimidazolium chloride (Bmim-Cl, 50.0 g) and high purity dry acetone (>99.5%, 500 ml) were combined in a 1 liter flask and warmed to reflux with magnetic stirring until the solid all dissolved. At room temperature in a separate 1 liter flask, potassium-1,1,2,3,3,3-hexafluoropropanesulfonte (HFPS-K) was dissolved in high purity dry acetone (550 ml). These two solutions were combined at room temperature and allowed to stir magnetically for 12 hr under positive nitrogen pressure. The stirring was stopped, and the KCl precipitate was allowed to settle. This solid was removed by suction filtration through a fritted glass funnel with a celite pad. The acetone was removed in vacuo to give a yellow oil. The oil was further purified by diluting with high purity acetone (100 ml) and stirring with decolorizing carbon (5 g). The mixture was suction filtered and the acetone removed in vacuo to give a colorless oil. This was further dried at 4 Pa and 25 degrees C. for 2 hr to provide 68.6 g of product.

$^{19}F$ NMR (DMSO-$d_6$) δ −73.8 (s, 3F); −114.5, −121.0 (ABq, J=258 Hz, 2F); −210.6 (m, J=42 Hz, 1F).

$^1H$ NMR (DMSO-$d_6$) δ 0.9 (t, J=7.4 Hz, 3H); 1.3 (m, 2H); 1.8 (m, 2H); 3.9 (s, 3H); 4.2 (t, J=7 Hz, 2H); 5.8 (dm, J=42 Hz, 1H); 7.7 (s, 1H); 7.8 (s, 1H); 9.1 (s, 1H).

% Water by Karl-Fisher titration: 0.12%.

Analytical calculation for $C_9H_{12}F_6N_2O_3S$: C, 35.7; H, 4.4; N, 7.6.

Experimental Results: C, 34.7; H, 3.8; N, 7.2.

TGA (air): 10% wt. loss @ 340 degrees C., 50% wt. loss @ 367 degrees C.

TGA ($N_2$): 10% wt. loss @ 335 degrees C., 50% wt. loss @ 361 degrees C.

Extractable chloride by ion chromatography: 27 ppm.

EXAMPLE 11

Synthesis of 1-butyl-3-methylimidazolium 1,12-trifluoro-2-(trifluoromethoxy)ethanesulfonate (Bmim-TTES) (Cation, imidazolium; Anion, Formula 1)

1-Butyl-3-methylimidazolium chloride (Bmim-Cl, 10.0 g) and deionized water (15 ml) were combined at room temperature in a 200 ml flask. At room temperature in a separate 200 ml flask, potassium 1,1,2-trifluoro-2-(trifluoromethoxy) ethanesulfonate (TTES-K, 16.4 g) was dissolved in deionized water (90 ml). These two solutions were combined at room temperature and allowed to stir magnetically for 30 min. under positive nitrogen pressure to give a biphasic mixture with the desired ionic liquid as the bottom phase. The layers were separated, and the aqueous phase was extracted with 2×50 ml portions of methylene chloride. The combined organic layers were dried over magnesium sulfate and concentrated in vacuo. The colorless oil product was dried at for 4 hr at 5 Pa and 25 degrees C. to afford 15.0 g of product.

$^{19}F$ NMR (DMSO-$d_6$) δ −56.8 (d, $J_{FH}$=4 Hz, 3F); −119.5, −119.9 (subsplit ABq, J=260 Hz, 2F); −142.2 (dm, $J_{FH}$=53 Hz, 1F).

$^1H$ NMR (DMSO-$d_6$) δ 0.9 (t, J=7.4 Hz, 3H); 1.3 (m, 2H); 1.8 (m, 2H); 3.9 (s, 3H); 4.2 (t, J=7.0 Hz, 2H); 6.5 (dt, J=53 Hz, J=7 Hz, 1H); 7.7 (s, 1H); 7.8 (s, 1H); 9.1 (s, 1H).

% Water by Karl-Fisher titration: 613 ppm.

Analytical calculation for C11H16F6N2O4S: C, 34.2; H, 4.2; N, 7.3.

Experimental Results: C, 34.0; H, 4.0; N, 7.1.

TGA (air): 10% wt. loss @ 328 degrees C., 50% wt. loss @ 354 degrees C.

TGA ($N_2$): 10% wt. loss @ 324 degrees C., 50% wt. loss @ 351 degrees C.

Extractable chloride by ion chromatography: <2 ppm.

EXAMPLE 12

Synthesis of 1-butyl-3-methylimidazolium 1,1,2-trifluoro-2-(perfluoroethoxy)ethanesulfonate (Bmim-TPES) (Cation, imidazolium; Anion, Formula 1)

1-Butyl-3-methylimidazolium chloride (Bmim-Cl, 7.8 g) and dry acetone (150 ml) were combined at room temperature in a 500 ml flask. At room temperature in a separate 200 ml flask, potassium 1,1,2-trifluoro-2-(perfluoroethoxy)ethanesulfonate (TPES-K, 15.0 g) was dissolved in dry acetone (300 ml). These two solutions were combined and allowed to stir magnetically for 12 hr under positive nitrogen pressure. The KCl precipitate was then allowed to settle leaving a colorless solution above it. The reaction mixture was filtered once through a celite/acetone pad and again through a fritted glass funnel to remove the KCl. The acetone was removed in vacuo first on a rotovap and then on a high vacuum line (4 Pa, 25 degrees C.) for 2 hr. Residual KCl was still precipitating out of the solution, so methylene chloride (50 ml) was added to the crude product which was then washed with deionized water (2×50 ml). The solution was dried over magnesium sulfate, and the solvent was removed in vacuo to give the product as a viscous light yellow oil (12.0 g, 62% yield).

$^{19}$F NMR (CD$_3$CN) δ −85.8 (s, 3F); −87.9, −90.1 (subsplit ABq, J$_{FF}$=147 Hz, 2F);

−120.6, −122.4 (subsplit ABq, J$_{FF}$=258 Hz, 2F); −142.2 (dm, J$_{FH}$=53 Hz, 1F).

$^1$H NMR (CD$_3$CN) δ 1.0 (t, J=7.4 Hz, 3H); 1.4 (m, 2H); 1.8 (m, 2H); 3.9 (s, 3H);

4.2 (t, J=7.0 Hz, 2H); 6.5 (dm, J=53 Hz, 1H); 7.4 (s, 1H); 7.5 (s, 1H); 8.6 (s, 1H).

% Water by Karl-Fisher titration: 0.461.

Analytical calculation for C12H16F8N2O4S: C, 33.0; H, 3.7.

Experimental Results: C, 32.0; H, 3.6.

TGA (air): 10% wt. loss @ 334 degrees C., 50% wt. loss @ 353 degrees C.

TGA (N$_2$): 10% wt. loss @ 330 degrees C., 50% wt. loss @ 365 degrees C.

EXAMPLE 13

Synthesis of tetradecyl(tri-n-butyl)phosphonium 1,1,2,3,3,3-hexafluoropropanesulfonate ([4.4.4.14]P-HFPS) (Cation, imidazolium; Anion, Formula 1)

To a 4l round bottomed flask was added the ionic liquid tetradecyl(tri-n-butyl)phosphonium chloride (Cyphos® IL 167, 345 g) and deionized water (1000 ml). The mixture was magnetically stirred until it was one phase. In a separate 2 liter flask, potassium 1,1,2,3,3,3-hexafluoropropanesulfonate (HFPS-K, 214.2 g) was dissolved in deionized water (1100 ml). These solutions were combined and stirred under positive N$_2$ pressure at 26 degrees C. for 1 hr producing a milky white oil. The oil slowly solidified (439 g) and was removed by suction filtration and then dissolved in chloroform (300 ml). The remaining aqueous layer (pH=2) was extracted once with chloroform (100 ml). The chloroform layers were combined and washed with an aqueous sodium carbonate solution (50 ml) to remove any acidic impurity. They were then dried over magnesium sulfate, suction filtered, and reduced in vacuo first on a rotovap and then on a high vacuum line (4 Pa, 100 degrees C.) for 16 hr to yield the final product as a white solid (380 g, 76% yield).

$^{19}$F NMR (DMSO-d$_6$) δ −73.7 (s, 3F); −114.6, −120.9 (ABq, J=258 Hz, 2F); −210.5 (m, J$_{HF}$=41.5 Hz, 1F).

$^1$H NMR (DMSO-d$_6$) δ 0.8 (t, J=7.0 Hz, 3H); 0.9 (t, J=7.0 Hz, 9H); 1.3 (br s, 20H); 1.4 (m, 16H); 2.2 (m, 8H); 5.9 (m, J$_{HF}$=42 Hz, 1H).

% Water by Karl-Fisher titration: 895 ppm.

Analytical calculation for C29H57F6O3PS: C, 55.2; H, 9.1; N, 0.0.

Experimental Results: C, 55.1; H, 8.8; N, 0.0.

TGA (air): 10% wt. loss @ 373 degrees C., 50% wt. loss @ 421 degrees C.

TGA (N$_2$): 10% wt. loss @ 383 degrees C., 50% wt. loss @ 436 degrees C.

EXAMPLE 14

Synthesis of Tetradecyl(tri-n-hexyl)phosphonium 1,1,2-trifluoro-2-(perfluoroethoxy)ethanesulfonate ([6.6.6.14]P-TPES) (Cation, imidazolium; Anion, Formula 1)

To a 500 ml round bottomed flask was added acetone (Spectroscopic grade, 50 ml) and ionic liquid tetradecyl(tri-n-hexyl)phosphonium chloride (Cyphos® IL 101, 33.7 g). The mixture was magnetically stirred until it was one phase. In a separate 1 liter flask, potassium 1,1,2-trifluoro-2-(perfluoroethoxy)ethanesulfonate (TPES-K, 21.6 g) was dissolved in acetone (400 ml). These solutions were combined and stirred under positive N$_2$ pressure at 26 degrees C. for 12 hr producing a white precipitate of KCl. The precipitate was removed by suction filtration, and the acetone was removed in vacuo on a rotovap to produce the crude product as a cloudy oil (48 g). Chloroform (100 ml) was added, and the solution was washed once with deionized water (50 ml). It was then dried over magnesium sulfate and reduced in vacuo first on a rotovap and then on a high vacuum line (8 Pa, 24 degrees C.) for 8 hr to yield the final product as a slightly yellow oil (28 g, 56% yield).

$^{19}$F NMR (DMSO-d$_6$) δ −86.1 (s, 3F); −88.4, −90.3 (subsplit ABq, J$_{FF}$=147 Hz, 2F); −121.4, −122.4 (subsplit ABq, J$_{FF}$=258 Hz, 2F); −143.0 (dm, J$_{FH}$=53 Hz, 1F).

$^1$H NMR (DMSO-d$_6$) δ 0.9 (m, 12H); 1.2 (m, 16H); 1.3 (m, 16H); 1.4 (m, 8H);

1.5 (m, 8H); 2.2 (m, 8H); 6.3 (dm, J$_{FH}$=54 Hz, 1H).

% Water by Karl-Fisher titration: 0.11.

Analytical calculation for C36H69F8O4PS: C, 55.4; H, 8.9; N, 0.0.

Experimental Results: C, 55.2; H, 8.2; N, 0.1.

TGA (air): 10% wt. loss @ 311 degrees C., 50% wt. loss @ 339 degrees C.

TGA (N$_2$): 10% wt. loss @ 315 degrees C., 50% wt. loss @ 343 degrees C.

EXAMPLE 15

Synthesis of tetradecyl(tri-n-hexyl)phosphonium 1,1,2-trifluoro-2-(trifluoromethoxy)ethanesulfonate ([6.6.6.14]P-TTES) (Cation, imidazolium; Anion, Formula 1)

To a 100 ml round bottomed flask was added acetone (Spectroscopic grade, 50 ml) and ionic liquid tetradecyl(tri-n-hexyl)phosphonium chloride (Cyphos® IL 101, 20.2 g). The mixture was magnetically stirred until it was one phase. In a separate 100 ml flask, potassium 1,1,2-trifluoro-2-(trifluoromethoxy)ethanesulfonate (TTES-K, 11.2 g) was dissolved in acetone (100 ml). These solutions were combined and stirred under positive N$_2$ pressure at 26 degrees C. for 12 hr producing a white precipitate of KCl.

The precipitate was removed by suction filtration, and the acetone was removed in vacuo on a rotovap to produce the crude product as a cloudy oil. The product was diluted with ethyl ether (100 ml) and then washed once with deionized water (50 ml), twice with an aqueous sodium carbonate solution (50 ml) to remove any acidic impurity, and twice more with deionized water (50 ml). The ether solution was then dried over magnesium sulfate and reduced in vacuo first on a rotovap and then on a high vacuum line (4 Pa, 24 degrees C.) for 8 hr to yield the final product as an oil (19.0 g, 69% yield).

$^{19}$F NMR (CD$_2$Cl$_2$) δ −60.2 (d, J$_{FH}$=4 Hz, 3F); −120.8, −125.1 (subsplit ABq, J=260 Hz, 2F); −143.7 (dm, J$_{FH}$=53 Hz, 1F).

$^1$H NMR (CD$_2$Cl$_2$) δ 0.9 (m, 12H); 1.2 (m, 16H); 1.3 (m, 16H); 1.4 (m, 8H); 1.5 (m, 8H); 2.2 (m, 8H); 6.3 (dm, J$_{FH}$=54 Hz, 1H).

% Water by Karl-Fisher titration: 412 ppm.

Analytical calculation for C35H69F6O4PS: C, 57.5; H, 9.5; N, 0.0.

Experimental results: C, 57.8; H, 9.3; N, 0.0.

TGA (air): 10% wt. loss @ 331 degrees C., 50% wt. loss @ 359 degrees C.

TGA (N$_2$): 10% wt. loss @ 328 degrees C., 50% wt. loss @ 360 degrees C.

EXAMPLE 16

Synthesis of 1-ethyl-3-methylimidazolium 1,1,2,2-tetrafluoro-2-(pentafluoroethoxy)sulfonate (Emim-TPENTAS) (Cation, imidazolium; Anion, Formula II)

To a 500 ml round bottomed flask was added 1-ethyl-3-methylimidazolium chloride (Emim-Cl, 98%, 18.0 g) and reagent grade acetone (150 ml). The mixture was gently warmed (50 degrees C.) until all of the Emim-Cl dissolved. In a separate 500 ml flask, potassium 1,1,2,2-tetrafluoro-2-(pentafluoroethoxy)sulfonate (TPENTAS-K, 43.7 g) was dissolved in reagent grade acetone (450 ml).

These solutions were combined in a 1 liter flask producing a white precipitate (KCl). The mixture was stirred at 24 degrees C. for 8 hr. The KCl precipitate was then allowed to settle leaving a clear yellow solution above it. The KCl was removed by filtration through a celite/acetone pad. The acetone was removed in vacuo to give a yellow oil which was then diluted with chloroform (100 ml). The chloroform was washed three times with deionized water (50 ml), dried over magnesium sulfate, filtered, and reduced in vacuo first on a rotovap and then on a high vacuum line (4 Pa, 25 degrees C.) for 8 hr. The product was a light yellow oil (22.5 g).

$^{19}$F NMR (DMSO-d$_6$) δ −82.9 (m, 2F); −87.3 (s, 3F); −89.0 (m, 2F); −118.9 (s, 2F).

$^1$H NMR (DMSO-d$_6$) δ 1.5 (t, J=7.3 Hz, 3H); 3.9 (s, 3H); 4.2 (q, J=7.3 Hz, 2H);

7.7 (s, 1H); 7.8 (s, 1H); 9.1 (s, 1H).

% Water by Karl-Fisher titration: 0.17%.

Analytical calculation for C10H11N2O4F9S: C, 28.2; H, 2.6; N, 6.6.

Experimental results: C, 28.1; H, 2.9; N, 6.6.

TGA (air): 10% wt. loss @ 351 degrees C., 50% wt. loss @ 401 degrees C.

TGA (N$_2$): 10% wt. loss @ 349 degrees C., 50% wt. loss @ 406 degrees C.

EXAMPLE 17

Synthesis of tetrabutylphosphonium 1,12-trifluoro-2-(perfluoroethoxy)ethanesulfonate (TBP-TPES) (Cation, phosphonium; Anion, Formula 1)

To a 200 ml round bottomed flask was added deionized water (100 ml) and tetra-n-butylphosphonium bromide (Cytec Canada Inc., 20.2 g). The mixture was magnetically stirred until the solid all dissolved. In a separate 300 ml flask, potassium 1,1,2-trifluoro-2-(perfluoroethoxy)ethanesulfonate (TPES-K, 20.0 g) was dissolved in deionized water (400 ml) heated to 70 degrees C. These solutions were combined and stirred under positive N$_2$ pressure at 26 degrees C. for 2 hr producing a lower oily layer. The product oil layer was separated and diluted with chloroform (30 ml), then washed once with an aqueous sodium carbonate solution (4 ml) to remove any acidic impurity, and three times with deionized water (20 ml). It was then dried over magnesium sulfate and reduced in vacuo first on a rotovap and then on a high vacuum line (8 Pa, 24 degrees C.) for 2 hr to yield the final product as a colorless oil (28.1 g, 85% yield).

$^{19}$F NMR (CD$_2$Cl$_2$) δ −86.4 (s, 3F); −89.0, −90.8 (subsplit ABq, J$_{FF}$=147 Hz, 2F);

−119.2, −125.8 (subsplit ABq, J$_{FF}$=254 Hz, 2F); −141.7 (dm, J$_{FH}$=53 Hz, 1F).

$^1$H NMR (CD$_2$Cl$_2$) δ 1.0 (t, J=7.3 Hz, 12H); 1.5 (m, 16H); 2.2 (m, 8H); 6.3 (dm, J$_{FH}$=54 Hz, 1H).

% Water by Karl-Fisher titration: 0.29.

Analytical calculation for C20H37F8O4PS: C, 43.2; H, 6.7; N, 0.0.

Experimental results: C, 42.0; H, 6.9; N, 0.1.

Extractable bromide by ion chromatography: 21 ppm.

EXAMPLE 18

Synthesis of (3,3,4,4,5,5,6,6,7,7,8,8,8-tridecafluorooctyl)-trioctylphosphonium 1,1,2,2-tetrafluoroethanesulfonate (Cation, phosphonium; Anion, Formula 1)

Trioctyl phosphine (31 g) was partially dissolved in reagent-grade acetonitrile (250 ml) in a large round-bottomed flask and stirred vigorously. 1,1,1,2,2,3,3,4,4,5,5,6,6-Tridecafluoro-8-iodooctane (44.2 g) was added, and the mixture was heated under reflux at 110 degrees C. for 24 hours. The solvent was removed under vacuum giving (3,3,4,4,5,5,6,6,7,7,8,8,8-tridecafluorooctyl)-trioctylphosphonium iodide as a waxy solid (30.5 g). Potassium 1,1,2,2-tetrafluoroethanesulfonate (TFES-K, 13.9 g) was dissolved in reagent grade acetone (100 ml) in a separate round-bottomed flask, and to this was added (3,3,4,4,5,5,6,6,7,7,8,8,8-tridecafluorooctyl)-trioctylphosphonium iodide (60 g). The reaction mixture was heated at 60 degrees C. under reflux for approximately 16 hours. The reaction mixture was then filtered using a large frit glass funnel to remove the white KI precipitate formed, and the filtrate was placed on a rotary evaporator for 4 hours to remove the acetone. The liquid was left for 24 hours at room temperature and then filtered a second time (to remove KI) to yield the product (62 g) as shown by proton NMR.

EXAMPLE 19

Synthesis of 1-methyl-3-(3,3,4,4,5,5,6,6,7,7,8,8,8-tridecafluorooctyl)imidazolium 1,1,2,2-tetrafluoroethanesulfonate (Cation, imidazolium; Anion, Formula 1)

1-Methylimidazole (4.32 g, 0.52 mol) was partially dissolved in reagent-grade toluene (50 ml) in a large round-bottomed flask and stirred vigorously. 1,1,1,2,2,3,3,4,4,5,5,6,6-Tridecafluoro-8-iodooctane (26 g, 0.053 mol) was added, and the mixture was heated under reflux at 110 degrees C. for 24 hours. The solvent was removed under vacuum giving 1-methyl-3-(3,3,4,4,5,5,6,6,7,7,8,8,8-tridecafluorooctyl) imidazolium iodide (30.5 g) as a waxy solid. Potassium 1,1, 2,2-tetrafluoroethanesulfonate (TFES-K, 12 g) was added to reagent grade acetone (100 ml) in a separate round-bottomed flask, and this solution was carefully added to the 1-methyl- 3-(3,3,4,4,5,5,6,6,7,7,8,8,8-tridecafluorooctyl)imidazolium iodide which had been dissolved in acetone (50 ml). The reaction mixture was heated under reflux for approximately 16 hours. The reaction mixture was then filtered using a large frit glass funnel to remove the white KI precipitate formed, and the filtrate was placed on a rotary evaporator for 4 hours to remove the acetone. The oily liquid was then filtered a second time to yield the product, as shown by proton NMR.

Examples 20-23 exemplify the polymerization of propanediol using the ionic liquids of the invention.

EXAMPLE 20

Polymerization of Propanediol 1,3-Propanediol (20 g) was placed in a three neck round bottomed flask. To this was added 1,1,2,2-tetrafluoroethanesulfonic acid (0.8 wt % in the final solution). The ionic liquid Bmim-TFES (4 g) was also added and the solution and contents were purged with nitrogen for two hours. The homogeneous solution was heated using an oil bath at 160 degrees C. under a nitrogen atmosphere. Water was slowly evolved and collected in a condenser. After approximately 9-10 hours the solution went from a single phase to a two-phase system. Upon cooling to 75 degrees C., two phases were clearly visible. The top phase was shown via NMR to be essentially polymerized propanediol (polyol). The molecular weight (Mn) was 2907, after a reaction time of 10.5 hours. The acid and ionic liquid were found to be essentially in the lower phase with polyol in the upper phase. The lower phase can easily be separated and recycled.

EXAMPLE 21

Polymerization of Propanediol 1,3-Propanediol (20 g) was placed in a three neck round bottomed flask. To this was added 1,1,2,2-tetrafluoroethanesulfonate (0.8 wt % in the final solution). The ionic liquid Emim-TFES (4 g) was also added and the solution and contents were purged with nitrogen for two hours. The homogeneous solution was heated using an oil bath at 160 degrees C. under a nitrogen atmosphere. Water was slowly evolved and collected in a condenser. After approximately 9-10 hours the solution went from a single phase to a two-phase system. Upon cooling to 75 degrees C., two phases were clearly visible. The top phase was shown via NMR to be essentially polymerized propanediol (polyol). The molecular weight (Mn) was 6131, after a reaction time of 10.5 hours. The acid and ionic liquid were found to be essentially in the lower phase with polyol in the upper phase. The lower phase can easily be separated and recycled.

EXAMPLE 22

Polymerization of Propanediol with Recycling of the Ionic Liquid 1,3-Propanediol (30 g) was placed in a three neck round bottomed flask. To this was added 1,1,2,3,3,3-hexafluoropropanesulfonic acid (0.15 g; 0.5 wt % in the final solution). The ionic liquid Bmim-TFES (2 g) was also added and the solution and contents were purged with nitrogen for two hours. The homogeneous solution was heated using an oil bath at 160 degrees C. under a nitrogen atmosphere. Water was slowly evolved and collected in a condenser. After approximately 26 hours the solution went from a single phase to a two-phase system. Upon cooling to 75 degrees C., two phases were clearly visible. The top phase was shown via NMR to be essentially polymerized propanediol (polyol). The molecular weight (Mn) was 2613, as determined using NMR. The total unsaturated ends was 30 meq/Kg. The acid and ionic liquid were found to be essentially in the lower phase with polyol in the upper phase.

A portion of the lower phase (2 g) was removed using a glass pipette. This was placed in a three neck round bottomed flask, followed by 28 g of 1,3-propanediol. The homogeneous solution was heated using an oil bath at 160 degrees C. under a nitrogen atmosphere. Water was slowly evolved and collected in a condenser. After approximately 30 hours the solution went from a single phase to a two-phase system. Upon cooling to 75 degrees C., two phases were clearly visible. The top phase was shown by NMR to be essentially polymerized propanediol (polyol). The molecular weight (Mn) was 3108 by NMR. The total unsaturated ends was 50 meq/Kg.

EXAMPLE 23

Polymerization of Propanediol 1,3-Propanediol was placed in a three neck round bottomed flask. To this was added 0.3 g of phosphotungstic acid (Aldrich) and 2 g of the ionic liquid Bmim-TFES; the solution and contents were purged with nitrogen for two hours. The homogeneous solution was heated using an oil bath at 160 degrees C. under a nitrogen atmosphere. Water was slowly evolved and collected in a condenser. After approximately 24 hours the solution went from a single phase to a two-phase system. Upon cooling to 75 degrees C., two phases were clearly visible. The top phase was shown by NMR to be essentially polymerized propanediol (polyol). The molecular weight (Mn) was 4319 by NMR. The total unsaturated ends was 81 meq/Kg.

The invention claimed is:

1. A composition of matter of the Formula $Z^+A^-$, wherein $Z^+$ is a cation of the formula below:

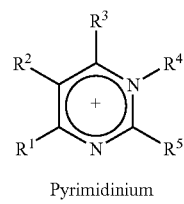

Pyrimidinium wherein $R^1$, $R^2$, $R^3$, $R^4$, and $R^5$ are independently selected from the group consisting of:
(i) H
(ii) halogen
(iii) —$CH_3$, —$C_2H_5$, or $C_3$ to $C_{25}$ straight-chain, branched or cyclic alkane or alkene, optionally substituted with at least one member selected from the group consisting of Cl, Br, F, I, OH, $NH_2$ and SH;
(iv) —$CH_3$, —$C_2H_5$, or $C_3$ to $C_{25}$ straight-chain, branched or cyclic alkane or alkene comprising one to three heteroatoms selected from the group consisting of O, N and S, and optionally substituted with at least one member selected from the group consisting of Cl, Br, F, I, OH, $NH_2$ and SH;

(v) $C_6$ to $C_{25}$ unsubstituted aryl or $C_6$ to $C_{25}$ unsubstituted heteroaryl having one to three heteroatoms independently selected from the group consisting of O, N and S; and (vi) $C_6$ to $C_{25}$ substituted aryl or $C_6$ to $C_{25}$ substituted heteroaryl having one to three heteroatoms independently selected from the group consisting of O, N and S; and wherein said substituted aryl or substituted heteroaryl has one to three substituents independently selected from the group consisting of:
  (1) —$CH_3$, —$C_2H_5$, or $C_3$ to $C_{25}$ straight-chain, branched or cyclic alkane or alkene, optionally substituted with at least one member selected from the group consisting of Cl, Br, F, I, OH, $NH_2$ and SH,
  (2) OH,
  (3) $NH_2$, and
  (4) SH; and wherein optionally at least two of $R^1$, $R^2$, $R^3$, $R^4$, and $R^5$ can together form a cyclic or bicyclic alkanyl or alkenyl group;

and $A^-$ is an anion selected from the group consisting of Formulae I, II and III:

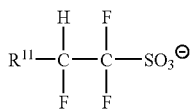

Formula I wherein:
$R^{11}$ is selected from the group consisting of:
  (1) halogen;
  (2) —$CH_3$, —$C_2H_5$ or $C_3$ to $C_{15}$ straight-chain or branched alkane or alkene, optionally substituted with at least one member selected from the group consisting of Cl, Br, I, OH, $NH_2$ and SH;
  (3) —$OCH_3$, —$OC_2H_5$ or $C_3$ to $C_{15}$ straight-chain or branched alkoxy, optionally substituted with at least one member selected from the group consisting of Cl, Br, I, OH, $NH_2$ and SH;
  (4) $C_1$ to $C_{15}$ straight-chain or branched fluoroalkyl, optionally substituted with at least one member selected from the group consisting of Cl, Br, I, OH, $NH_2$ and SH;
  (5) $C_1$ to $C_{15}$ straight-chain or branched fluoroalkoxy, optionally substituted with at least one member selected from the group consisting of Cl, Br, I, OH, $NH_2$ and SH;
  (6) $C_1$ to $C_{15}$ straight-chain or branched perfluoroalkyl; and
  (7) $C_1$ to $C_{15}$ straight-chain or branched perfluoroalkoxy;

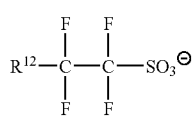

Formula II wherein:
$R^{12}$ is selected from the group consisting of:
  (1) —$CH_3$, —$C_2H_5$ or $C_3$ to $C_{15}$ straight-chain or branched alkoxy, optionally substituted with at least one member selected from the group consisting of Cl, Br, I, OH, $NH_2$ and SH;
  (2) $C_1$ to $C_{15}$ straight-chain or branched fluoroalkoxy, optionally substituted with at least one member selected from the group consisting of Cl, Br, I, OH, $NH_2$ and SH; and
  (3) $C_1$ to $C_{15}$ straight-chain or branched perfluoroalkoxy; and

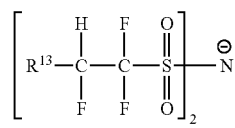

Formula III wherein:
$R^{13}$ is selected from the group consisting of:
  (1) halogen;
  (2) —$CH_3$, —$C_2H_5$ or $C_3$ to $C_{15}$ straight-chain or branched alkane or alkene, optionally substituted with at least one member selected from the group consisting of Cl, Br, I, OH, $NH_2$ and SH;
  (3) —$OCH_3$, —$OC_2H_5$ or $C_3$ to $C_{15}$ straight-chain or branched alkoxy, optionally substituted with at least one member selected from the group consisting of Cl, Br, I, OH, $NH_2$ and SH;
  (4) $C_1$ to $C_{15}$ straight-chain or branched fluoroalkyl, optionally substituted with at least one member selected from the group consisting of Cl, Br, I, OH, $NH_2$ and SH;
  (5) $C_1$ to $C_{15}$ straight-chain or branched fluoroalkoxy, optionally substituted with at least one member selected from the group consisting of Cl, Br, I, OH, $NH_2$ and SH;
  (6) $C_1$ to $C_{15}$ straight-chain or branched perfluoroalkyl; and
  (7) $C_1$ to $C_{15}$ straight-chain or branched perfluoroalkoxy.

2. The composition of claim 1 wherein the anion is 1,1,2,2-tetrafluoroethanesulfonate; 2-chloro-1,1,2-trifluoroethanesulfonate; 1,1,2,3,3,3-hexafluoropropanesulfonate; 1,1,2-trifluoro-2-(trifluoromethoxy)ethanesulfonate; 1,1,2-trifluoro-2-(pentafluoroethoxy)ethanesulfonate; 2-(1,2,2,2-tetrafluoroethoxy)-1,1,2,2-tetrafluoroethanesulfonate; 2-(1,1,2,2-tetrafluoroethoxy)-1,1,2,2-tetrafluoroethanesulfonate; 2-(1,1,2,2-tetrafluoro-2-iodoethoxy)-1,1,2,2-tetrafluoroethanesulfonate; 1,1,2,2-tetrafluoro-2-(pentafluoroethoxy)ethanesulfonate; N,N-bis(1,1,2,2-tetrafluoroethanesulfonyl)imide; or N,N-bis(1,1,2,3,3,3-hexafluoropropanesulfonyl)imide.

* * * * *